US009158890B2

(12) United States Patent
Meredith et al.

(10) Patent No.: US 9,158,890 B2
(45) Date of Patent: Oct. 13, 2015

(54) MOBILE APPLICATIONS AND METHODS FOR CONVEYING PERFORMANCE INFORMATION OF A CARDIAC PACEMAKER

(75) Inventors: Sheldon Kent Meredith, Roswell, GA (US); Brandon Bowers Hilliard, Woodstock, GA (US); Mario B. Kosseifi, Roswell, GA (US)

(73) Assignee: AT&T MOBILITY II LLC, Atlanta, GA (US)

( * ) Notice: Subject to any disclaimer, the term of this patent is extended or adjusted under 35 U.S.C. 154(b) by 327 days.

(21) Appl. No.: 13/191,996

(22) Filed: Jul. 27, 2011

(65) Prior Publication Data

US 2013/0030494 A1    Jan. 31, 2013

(51) Int. Cl.
*A61N 1/372* (2006.01)
*A61N 1/37* (2006.01)
*G06F 19/00* (2011.01)
(Continued)

(52) U.S. Cl.
CPC .......... *G06F 19/3412* (2013.01); *A61B 5/0028* (2013.01); *A61B 5/0031* (2013.01); *A61B 5/0205* (2013.01); *A61N 1/3706* (2013.01); *A61N 1/3727* (2013.01); *G06F 19/3418* (2013.01); *G06F 19/3481* (2013.01); *A61B 5/02438* (2013.01); *A61B 5/145* (2013.01); *A61B 2505/07* (2013.01); *A61B 2560/0204* (2013.01); *A61B 2560/0271* (2013.01); *A61N 1/3708* (2013.01)

(58) Field of Classification Search
CPC .............. A61N 1/3706; A61N 1/3712; A61N 1/36514; A61N 1/3702; A61N 1/37211; A61N 1/37247

USPC ....................................................... 607/32, 60
See application file for complete search history.

(56) References Cited

U.S. PATENT DOCUMENTS 5,394,879 A * 3/1995 Gorman ........................ 600/520
5,792,202 A * 8/1998 Rueter ............................ 607/27
(Continued)

OTHER PUBLICATIONS

Mike Miliard, Philips launches 24/7 pacemaker monitoring, Healthcare IT News, Nov. 22, 2010, http://www.healthcareitnews.com/news/philips-launches-247-pacemaker-monitoring.
(Continued)

*Primary Examiner* — Michael Kahelin
*Assistant Examiner* — Minh Duc Pham
(74) *Attorney, Agent, or Firm* — Guntin & Gust, PLC; Jay H. Anderson (57) ABSTRACT

Devices, systems, and methods are disclosed for relaying information from a cardiac pacemaker to an external device. Logic on the pacemaker modulates a heartbeat clock of the pacemaker to encode information onto a blood pressure sequence. This is accomplished by adding or subtracting a small subinterval to or from a pulse repetition interval of the pacemaker. A muscle stimulator beats the heart according to the modulated sequence. A monitoring device external to the body monitors the blood pressure to retrieve the encoded information, or message. The encoded information is then decoded to determine the information in the message. This information may concern the pacemaker as well as other devices within the body that are in communication with the pacemaker such as blood monitors, etc. Since the message is conveyed via simple modulation of the heart beat intervals, no separate transmitter is required in the pacemaker which would otherwise increase cost and decrease battery life.

12 Claims, 6 Drawing Sheets

(51) Int. Cl.
*A61B 5/0205* (2006.01)
*A61B 5/00* (2006.01)
*A61B 5/024* (2006.01)
*A61B 5/145* (2006.01)

(56) References Cited

U.S. PATENT DOCUMENTS

| | | |
|---|---|---|
| 5,871,451 A | 2/1999 | Unger |
| 6,236,889 B1 | 5/2001 | Soykan |
| 6,490,487 B1 | 12/2002 | Kraus |
| 6,553,262 B1 | 4/2003 | Feucht |
| 6,574,509 B1 | 6/2003 | Kraus |
| 7,138,902 B2 | 11/2006 | Menard |
| 7,198,603 B2 | 4/2007 | Penner |
| 7,962,210 B2 | 6/2011 | Daum |
| 2004/0078065 A1* | 4/2004 | Kroll .............................. 607/60 |
| 2004/0199212 A1 | 10/2004 | Fischell |
| 2004/0220639 A1* | 11/2004 | Mulligan et al. ................ 607/28 |
| 2006/0159074 A1 | 7/2006 | Diebold |
| 2007/0032832 A1 | 2/2007 | Feher |
| 2007/0142728 A1 | 6/2007 | Penner |
| 2008/0086176 A1 | 4/2008 | Ofek |
| 2009/0240308 A1 | 9/2009 | Feher |
| 2010/0094367 A1 | 4/2010 | Sen |
| 2011/0029029 A1 | 2/2011 | Leibsohn |

OTHER PUBLICATIONS

Gene Ostrovsky, Continuuos ECG Monitoring on an Android Phone, medGadget, Oct. 7, 2010, http://medgadget.com/2010/10/continuous_ecg_monitoring_on_an_android_phone.html.

Gene Ostrovksy, ECG Attachment for Your iPhone, medGadget, Dec. 30, 2010, http://medgadget.com/2010/12/ecg_attachment_for_your_iphone.html.

* cited by examiner

MOBILE APPLICATIONS AND METHODS FOR CONVEYING PERFORMANCE INFORMATION OF A CARDIAC PACEMAKER

BACKGROUND OF THE SUBJECT DISCLOSURE

1. Field of the Subject Disclosure

The subject disclosure relates to pacemakers. In particular, the subject disclosure relates to pacemakers for conveying performance information of a cardiac pacemaker to an external device.

2. Background of the Subject Disclosure

Recipients of cardiac pacemakers are occasionally required to visit their doctors to check up on the performance of their installed pacemakers along with a general check up. The doctor uses devices that can communicate with a pacemaker inductively, i.e. without the need to intrude through skin or other tissues. The devices retrieve performance information from the pacemaker, including battery charge level and any errors in the software controlling the pacemaker. Such equipment is highly specialized, expensive to acquire and expensive to operate with a trained specialist. When not at a medical facility with such equipment and specialists, the pacemaker's performance cannot be remotely monitored. Any sudden onset of performance issues, such as a battery draining at an abnormal rate, may present a life threatening situation that is undetected until it is too late to take action.

Mobile devices, such as cellular telephones, have become a common tool of everyday life. Cellular telephones are no longer used simply to place telephone calls. With the number of available features rapidly increasing, cellular telephones are now used for storing addresses, keeping a calendar, reading e-mails, drafting documents, etc. These devices are small enough that they can be carried in a pocket or purse all day, allowing a patient to stay in contact almost anywhere. Recent devices have become highly functional, providing applications useful to business professionals as well as the casual patient.

Mobile devices are frequently used for sending and receiving messages. Such devices may, for instance, send basic text messages using Short Message Service (SMS) and enhanced messages using Multimedia Messaging Service (MMS). Unfortunately, nowadays, the number of abilities also allows mobile devices to introduce new malware propagation vectors such as SMS/MMS messaging and file transfers. MMS messages can embed text, audio, images and video. However, none of these messaging capabilities have been applied to cardiac pacemakers.

On a worldwide basis there are 3 million people with pacemakers now and it is growing by 600,000 per year and accelerating. Therefore, what are needed are improved devices, systems, and methods to collect and analyze information from a cardiac pacemaker.

SUMMARY OF THE SUBJECT DISCLOSURE

The subject disclosure presents devices, systems, and methods for relaying information from a cardiac pacemaker to an external device. In exemplary embodiments, logic on the pacemaker modulates a heartbeat clock of the pacemaker to encode information onto a blood pressure sequence. This is accomplished by adding or subtracting a small subinterval to or from a pulse repetition interval of the pacemaker. A muscle stimulator beats the heart according to the modulated sequence. A monitoring device external to the body monitors the blood pressure to retrieve the encoded information, or message. The encoded information is then decoded to determine the information in the message. This information may concern the pacemaker as well as other devices within the body that are in communication with the pacemaker such as blood monitors, etc. Since the message is conveyed via simple modulation of the heart beat intervals, no separate transmitter is required in the pacemaker which would otherwise increase cost and decrease battery life.

The pacemaker performance information may be transmitted to medical entities on a daily basis rather than having to wait for extended intervals between checkups. Potential problems with the pacemaker or its battery are identified much faster, thereby avoiding a life threatening condition. Exemplary embodiments require no more energy than used by existing pacemakers, and do not require a physical redesign. A software modification enables the pacemaker to transmit information through the patient's heartbeat. This reduces the frequency of doctor's appointments, resulting in lower cost to the patient, less strain on medical institutions, lower insurance premiums, and enhanced profit margins for medical entities. Further, the rapidly increasing portion of the population that currently has pacemakers can immediately benefit from the devices and mobile applications disclosed herein.

In one exemplary embodiment, the subject disclosure is a method for communicating information through a heartbeat. The method includes applying a standard interval clock to stimulate a heartbeat, modifying an interval of the standard interval clock by one of adding and subtracting a subinterval to represent a binary digit, and stimulating a heart muscle according to the modified interval.

In another exemplary embodiment, the subject disclosure is a device for communicating information through a heartbeat. The device includes a standard interval clock for stimulating a heartbeat, a clock modulator for modifying an interval of the standard interval clock by one of adding and subtracting a subinterval to represent a binary digit, and a muscle stimulator for stimulating a heart muscle according to the modified interval.

In yet another exemplary embodiment, the subject disclosure is a system for communicating information through a heartbeat. The system includes a pacemaker for applying a standard interval clock to stimulate a heartbeat, modifying an interval of the standard interval clock by one of adding and subtracting a subinterval to represent a binary digit, and stimulating a heart muscle according to the modified interval, and a pulse monitor for receiving the binary digit from the heartbeat.

DETAILED DESCRIPTION OF THE SUBJECT DISCLOSURE

Exemplary embodiments of the subject disclosure include a pacemaker that inserts small deviations in the timing of each heart beat to communicate information. For example, assume the normal period of a heart beat controlled by the pacemaker is exactly sixty beats per minute, or one beat per second exactly. This interval is then modified by a subinterval to convey information about the performance of the pacemaker. For instance, an interval of 0.95 seconds could imply a binary zero while an interval of 1.05 seconds could imply a binary one. In this instance, a subinterval of 0.05 has been added or subtracted to create the binary integer. At an overall average interval of 60 beats per minute, the pacemaker conveys 60 bits of information per minute, and 3600 bits of information per hour. This is likely sufficient to convey most or all of the performance information needed including battery life and performance information for any attached devices. The timing of pulses, or heartbeats, conveys information while jointly serving the purpose of causing the heart beat. To receive this information, or message, a simple and inexpensive systolic blood pressure sensor is placed on the body of the patient. The blood pressure sensor outputs the information through either a wired or wireless connection, such as ETHERNET, BLUETOOTH, WIFI, ZIGBEE, Z-WAVE, etc. The blood pressure sensor uses this connection to communicate across a network, e.g., through a mobile device across a cellular network, to a remote application hosted on an application server accessible by a medical professional. The hosted application monitors the performance information from the message and determines if any performance degradations have occurred. Medical professionals, such as physicians, nurses, etc., also monitor performance and contact the patient or pacemaker owner to schedule a more thorough investigation at a medical facility, if needed.

Exemplary embodiments comprise a mobile device with at least a BLUETOOTH or equivalent transceiver, a cardiac pacemaker, a blood pressure sensor with BLUETOOTH or equivalent transceiver, and a remote application server including a remote application. Performance information of the pacemaker is relayed to the blood pressure sensor through a simple pulse code modulation scheme and then transmitted to a medical entity's remote server for remote diagnostics and proactive discovery of life-threatening performance problems.

"Pacemaker", as used herein and throughout this disclosure, refers to a medical device that uses electrical impulses, delivered by electrodes contacting the heart muscles, to regulate the beating of the heart. "Pulse" or "blood pressure sequence", refers to the beating of the heart. While many pacemakers use a single electrode, pacemakers equipped with multiple electrodes may stimulate different points within the heart to improve synchronization of the heart muscles.

"Mobile device", as used herein and throughout this disclosure, refers to any electronic device capable of wirelessly sending and receiving data. A mobile device may have a processor, a memory, a transceiver, an input, and an output. Examples of such devices include cellular telephones, personal digital assistants (PDAs), portable computers, etc. The memory stores applications, software, or logic. Examples of processors are computer processors (processing units), microprocessors, digital signal processors, controllers and microcontrollers, etc. Examples of device memories that may comprise logic include RAM (random access memory), flash memories, ROMS (read-only memories), EPROMS (erasable programmable read-only memories), and EEPROMS (electrically erasable programmable read-only memories).

"Logic" as used herein and throughout this disclosure, refers to any information having the form of instruction signals and/or data that may be applied to direct the operation of a processor. Logic may be formed from signals stored in a device memory. Software is one example of such logic. Logic may also be comprised by digital and/or analog hardware circuits, for example, hardware circuits comprising logical AND, OR, XOR, NAND, NOR, and other logical operations. Logic may be formed from combinations of software and hardware. On a network, logic may be programmed on a server, or a complex of servers. A particular logic unit is not limited to a single logical location on the network.

Mobile devices communicate with each other and with other elements via a network, for instance, a wireless network, or a wireline network. A "network" can include broadband wide-area networks such as cellular networks, local-area networks (LAN), and personal area networks, such as near-field communication (NFC) networks including BLUETOOTH®. Communication across a network is preferably packet-based; however, radio and frequency/amplitude modulations networks can enable communication between mobile devices using appropriate analog-digital-analog converters and other elements.

Communication is enabled by hardware elements called "transceivers." Mobile devices may have more than one transceiver, capable of communicating over different networks. For example, a cellular telephone can include a cellular transceiver for communicating with a cellular base station, a Wi-Fi transceiver for communicating with a Wi-Fi network, and a BLUETOOTH® transceiver for communicating with a BLUETOOTH® device. A network typically includes a plurality of elements that host logic for performing tasks on the network.

In modern packet-based wide-area networks, servers may be placed at several logical points on the network. Servers may further be in communication with databases and can enable mobile devices to access the contents of a database. Billing servers, application servers, etc. are examples of such servers. A server can include several network elements, including other servers, and can be logically situation anywhere on a service provider's network, such as the back-end of a cellular network. A server hosts or is in communication with a database hosting an account for a patient of a mobile device. The "patient account" includes several attributes for a particular patient, including a unique identifier of the mobile device(s) owned by the patient, relationships with other patients, application usage, location, personal settings, business rules, bank accounts, and other information. A server may communicate with other servers on different networks to update a patient account.

For the following description, it can be assumed that most correspondingly labeled structures across the figures (e.g., 120 and 220, etc.) possess the same characteristics and are subject to the same structure and function. If there is a difference between correspondingly labeled elements that is not pointed out, and this difference results in a non-corresponding structure or function of an element for a particular embodiment, then that conflicting description given for that particular embodiment shall govern.

Figure 1:
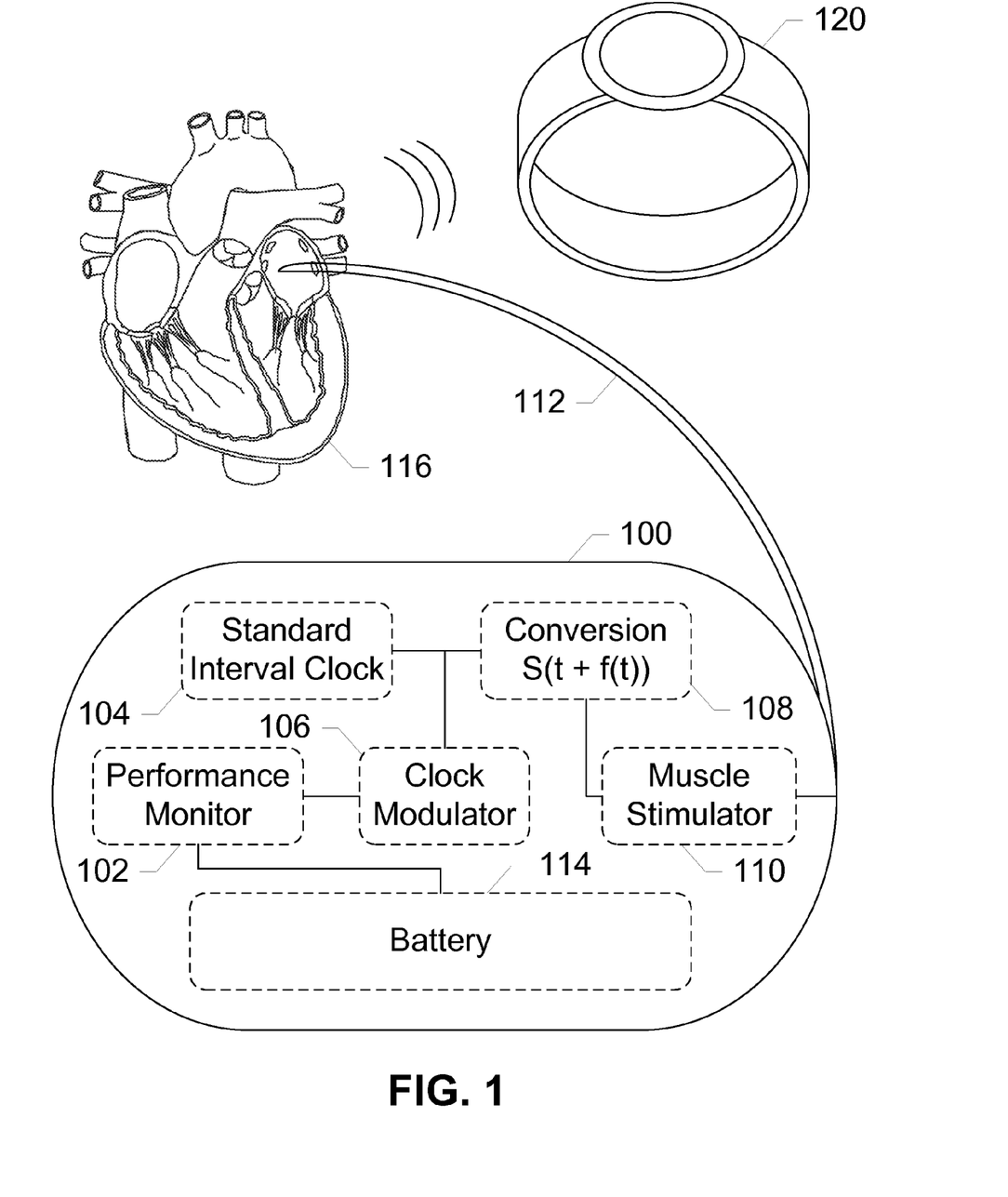
FIG. 1 shows a system for transferring information from a cardiac pacemaker, according to an exemplary embodiment of the subject disclosure.

FIG. 1 shows a system for transferring information from a cardiac pacemaker 100, according to an exemplary embodiment of the subject disclosure. The system includes cardiac pacemaker 100 controlling a heart 116 of a patient, and a monitoring device 120. Cardiac pacemaker 100 includes a performance monitor 102, a standard interval clock 104, a clock modulator 106, conversion logic 108, a muscle stimulator 110, an electrode 112, and a battery 114. Standard interval clock 104 produces a standard interval of time that triggers muscle stimulator 110 to send an electrical impulse. Performance monitor 102 monitors the functioning of the components of cardiac pacemaker 100, such as an amount of charge remaining on battery 114. Performance monitor 102 may further monitor any device in communication with cardiac pacemaker 100. When information detected by performance monitor 102 needs to be reported, clock modulator 106 generates a modulation signal representing the information to be reported. Conversion logic 108 modulates the signal using standard interval clock 104 to encode the information. This modulation slightly increases or decreases each of the standard intervals to encode the information onto the impulse interval. For instance, clock modulator 106 may slightly increase the standard interval to represent the binary integer '1' and slightly decrease the standard interval to represent the binary integer '0'. A combination of '1's and '0's over a series of impulse intervals sends encoded information to muscle stimulator 110.

Muscle stimulator 110 of cardiac pacemaker 100 is electrically coupled to an electrode 112 that extends into the sinoatrial node of heart 116. Muscle stimulator 110 sends an electrical impulse through electrode 112 to cause heart 116 to beat according to the modulated signal. The information, or message, encoded onto the impulse interval is reflected in the heartbeat, and consequently, the pulse or blood-pressure sequence includes this message. The pulse or blood-pressure sequence created by heart 116 is read by monitoring device 120. Monitoring device 120 may be, for instance, a pulse monitor, a mobile device capable of reading a pulse, a blood pressure monitor, etc.

In other exemplary embodiments, the pacemaker is equipped with a memory and processor. The memory contains logic for performing all of the functions of the performance monitor 102, standard interval clock 104, clock modulator 106, and conversion logic 108 of pacemaker 100. Using software to perform the functions may require more power to operate, but benefits from the ability to update the logic on the memory without replacing any hardware. Further, although a pacemaker is shown inserted into a human heart, exemplary embodiments of the pacemaker can be used in any animal.

As described above, the difference between a standard interval and a modified interval is the addition or subtraction of a subinterval. In exemplary embodiments, the subinterval is significantly less than the standard interval, such as one-twentieth (1/20) of the standard interval. Variations in human behavior may cause the pulse monitor to pick up pulse intervals that are skewed from what was intended. For instance, the patient may cough, or be engaged in strenuous activity. Exemplary embodiments of the pulse monitor use block error checking, cyclic redundancy checking, trellis coding, etc. to compensate for these variations and improve the accuracy of the performance information.

In further embodiments, the performance is scheduled to be monitored and transmitted to a systolic blood pressure sensor during sleep or any other time where body movements are minimal or otherwise do not result in a misreading of pressure. This avoids errors caused by the sinoatrial node of the heart causing contractions at a rate faster than otherwise provided by the pacemaker. Such errors may be further minimized using error checking and recovery, as explained herein. Use of such schemes reduces the information content per cardiac pulse by up to half, while retaining sufficient information volume to indicate the performance of the cardiac pacemaker.

Figure 2:
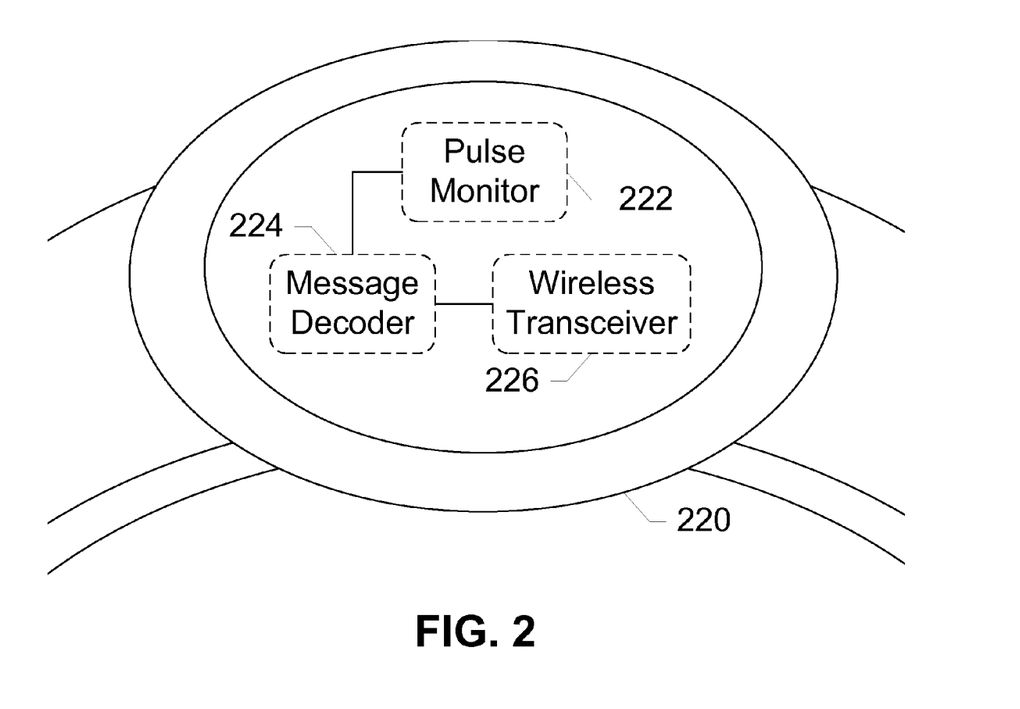
FIG. 2 shows a monitoring device, according to an exemplary embodiment of the subject disclosure.

FIG. 2 shows a monitoring device 220, according to an exemplary embodiment of the subject disclosure. Monitoring device 220 includes a pulse monitor 222, a message decoder 224, and a wireless transceiver 226. Pulse monitor 220 may be worn or placed around the wrist, chest, or any other location on a patient where a pulse or heartbeat may be detected. Pulse monitor 222 detects the pulse of the patient and measures the timing of the pulse to a degree or resolution where modulated intervals are distinguishable from unmodulated intervals. In other words, the resolution of the pulse monitor must be high enough to distinguish modulated intervals from unmodulated intervals. These measurements are sent to message decoder 224. Message decoder 224 contains logic to decode a message from the binary encoded pulse of the patient. Slight deviations to a standard pulse interval encoded by a cardiac pacemaker create this binary message that is decoded by message decoder 224. The decoded message is then sent to wireless transceiver 226. Wireless transceiver 226 may be a BLUETOOTH transceiver, may be a cellular transceiver, etc., and communicates the message to a mobile device, to a wireline device, to a physician center, etc.

In exemplary embodiments of the subject disclosure, the pulse is detected through any type of pulse detection. Many devices are used today to determine pulse, from stethoscopes to more sophisticated technologies including touch screen technology, etc. Many of these require constant contact with the skin, hence any wearable embodiment will become apparent to those of ordinary skill in the art in light of this disclosure.

In exemplary embodiments of the subject disclosure, the pulse monitor may lack a message decoder. In these embodiments, the pulse or blood pressure sequence is monitored and stored on a memory. The stored information may then be transmitted to a mobile device having decoding logic therein, or to a physician center where it is decoded. In embodiments of the subject disclosure, the pulse monitor further includes a display. In these embodiments, after the message is decoded, it is visible on the display. Thus, the patient is notified almost instantly of any status concerning the cardiac pacemaker or any device in communication with the cardiac pacemaker. In embodiments of the pulse monitor lacking a message decoder, the message may be decoded by the mobile device, physician center, etc., and sent back to the pulse monitor for display.

According to further embodiments of the subject disclosure, the monitoring device may itself be connected to a telephone line. In these embodiments, the monitoring device uses the telephone line to send the encoded or decoded message to another device, to a physician center, etc.

Figure 3:
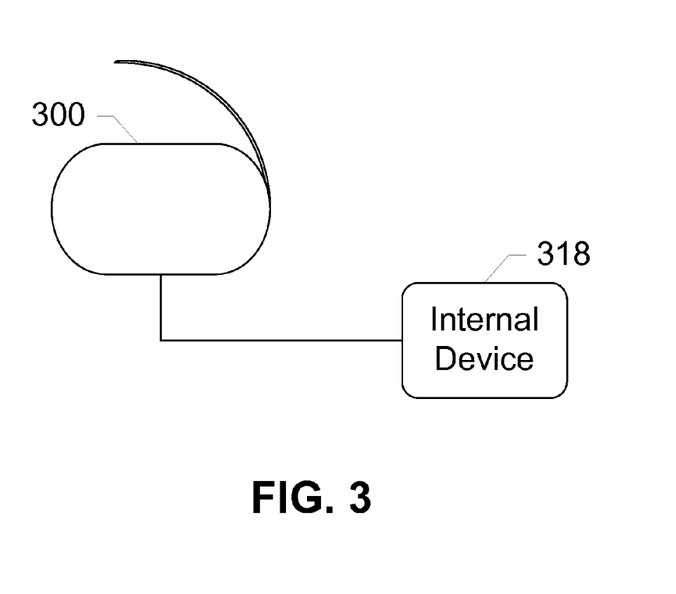
FIG. 3 shows an internal device coupled to a cardiac pacemaker, according to an exemplary embodiment of the subject disclosure.

FIG. 3 shows an internal device 318 coupled to a cardiac pacemaker 300, according to an exemplary embodiment of the subject disclosure. In this embodiment, internal device 318 is within a patient's body. Internal device 318 monitors or tests one or more measurable aspects of the patient's body, including but not limited to blood/sugar, cholesterol, insulin, iron, or any other measurable aspect of the patient's body. Internal device 318 sends this information to cardiac pacemaker 300 through an electric coupling to cardiac pacemaker 300. A clock modulator within cardiac pacemaker 300 modulates the standard interval to encode this information into the pulse of the patient to be read by a pulse or blood pressure meter as described herein.

In exemplary embodiments, virtually any device may be in communication with the pacemaker. Because the pacemaker does not have a wireless transceiver, the communication needs to be wired. Non-medical devices may be used as well, such as GPS implants, etc.

Figure 4:
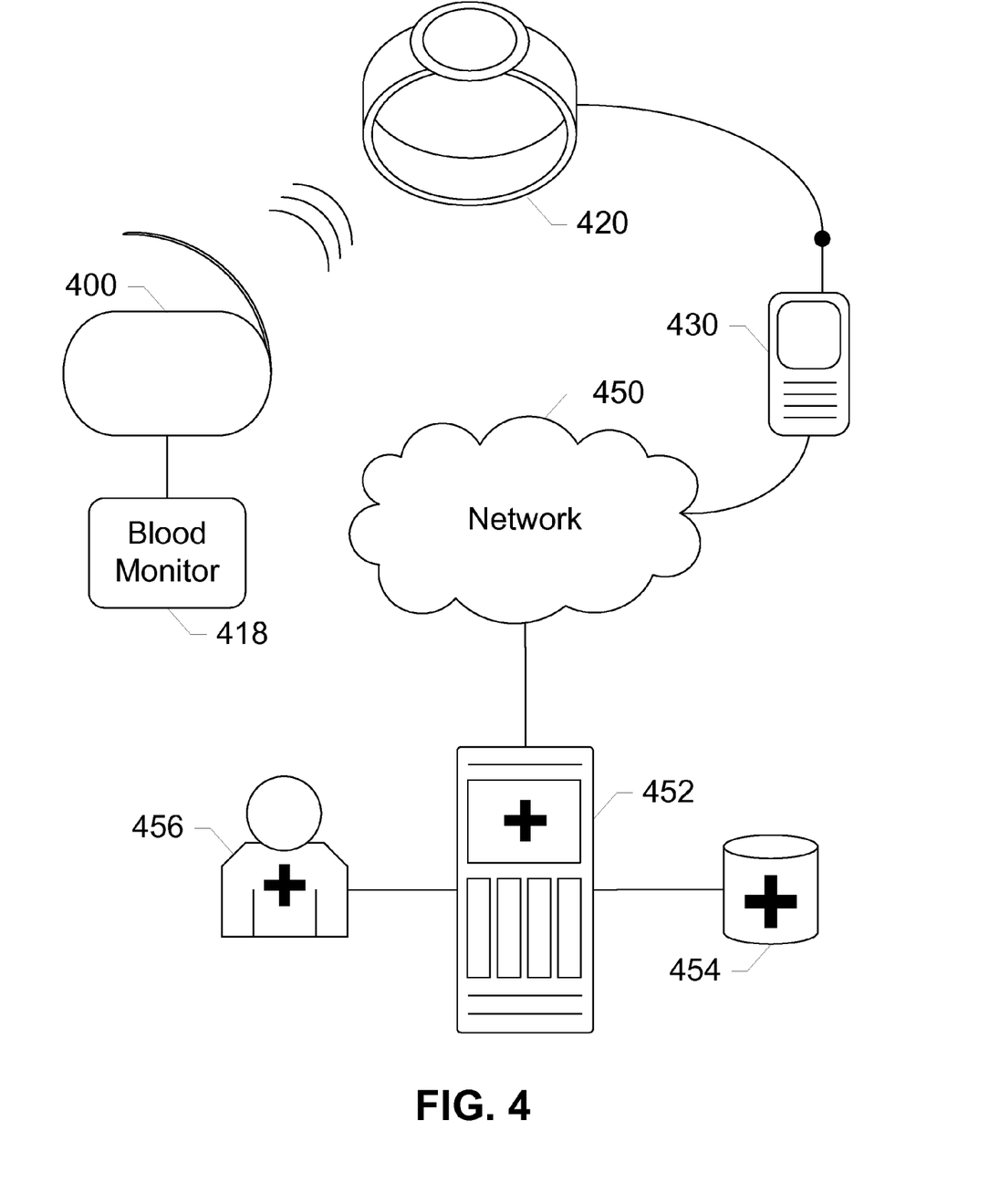
FIG. 4 shows a system for transferring information from a patient to a physician center, according to an exemplary embodiment of the subject disclosure.

FIG. 4 shows a system for transferring information from a patient to a physician center, according to an exemplary embodiment of the subject disclosure. In this embodiment, the system includes a cardiac pacemaker 400, a blood monitor 418, a pulse monitor 420, a mobile device 430, a network 450, a physician server 452, a physician database 454, and a physician 456. Pacemaker 400 delivers performance information through the pulse of its patient as described with respect to the several embodiments disclosed herein. Pacemaker 400 also communicates with blood monitor 418 to receive performance and diagnostic information. This information is received by pacemaker 400 and communicated via the pulse.

Pacemaker 400 wirelessly communicates the information to pulse monitor 420, which detects the pulse of the patient and measures the timing of the pulse to a degree, or resolution, where modulated intervals are distinguishable from unmodulated intervals. A message can be decoded once enough modulated intervals are received. The message contains diagnostics, performance information, maintenance information, etc. Pulse monitor 420 forwards this message to mobile device 430. Mobile device 430 reads the message, determines if any action or functions are to be executed, and executes any actions or functions based on the content of the message, such as alerting the patient, activating a GPS receiver to determine a location of the patient, etc.

Mobile device 430 then forwards the message to physician server 452 via network 450. Network 450 may be a cellular network, local area network, WiFi network, personal area network (PAN), or any other communication network. Physician server 452 processes the message by adding new information to physician database 454, and analyzing the information for further action. If the contents of a message warrant an action, the message may be flagged as needing attention from physician 456. Physician 456 monitors the results of the analysis of physician server 452, and alerts patients of any actions that need to be performed, such as providing a course of treatment, or scheduling an in-person diagnosis or medical test. Physician database 454 further stores these messages and any additional diagnostic information so that trends and statistics can be computed over time.

In other embodiments, additional devices such as glucose monitors, blood oxygen sensors, etc. are in wired communication with the pacemaker within or external to the patient's body. In some embodiments, the pulse monitor includes logic to analyze the message and perform a task based on the message. For example, if the pulse monitor receives a message indicating a low pacemaker charge, the pulse monitor alerts the user immediately. In this way, the mobile device is not required for simple alerts, but can still be used to forward information to the physician server. The pulse monitor may have additional equipment to announce alerts such as a speaker or display.

In exemplary embodiments of the subject disclosure, network 450 is a cellular network. A cellular network provides access to a wide-area radio network for communication between devices in different locations, such as mobile device 430 and physician server 452. Service providers such as wireless carriers typically provide service to a geographic market area by dividing the area into many smaller areas or cells. Each cell is serviced by a radio transceiver. Base transceiver stations connect to other elements of the cellular network that are known in the art and therefore not shown. For instance, base transceiver stations connect to Mobile Switching Centers (MSCs) through landlines, gateways, or other communication links, and the MSCs may, in turn, be connected via landlines to the Public Switched Telephone Network (PSTN), to other cellular networks, to IP networks, etc. Many other components are present in the cellular network, but are not presented for sake of simplicity. These components will be apparent to one of ordinary skill in the art in light of this disclosure.

In further embodiments, the messages are sent to a home medical server. A home medical server is located at the patients dwelling and can perform a greater analysis than the mobile device may be capable of. The home medical server may also serve as a backup of the physician server. Messages may be sent virtually anywhere on the network to be stored. In some exemplary embodiments, the mobile device is in communication with physician software within either or both of the mobile device and the physician server for processing and analyzing the information. A physician is used as an example in FIG. 4. However, many medical professionals can be used to monitor health information. In some cases, specialists are used to monitor a specific aspect of a patient's health.

Figure 5:
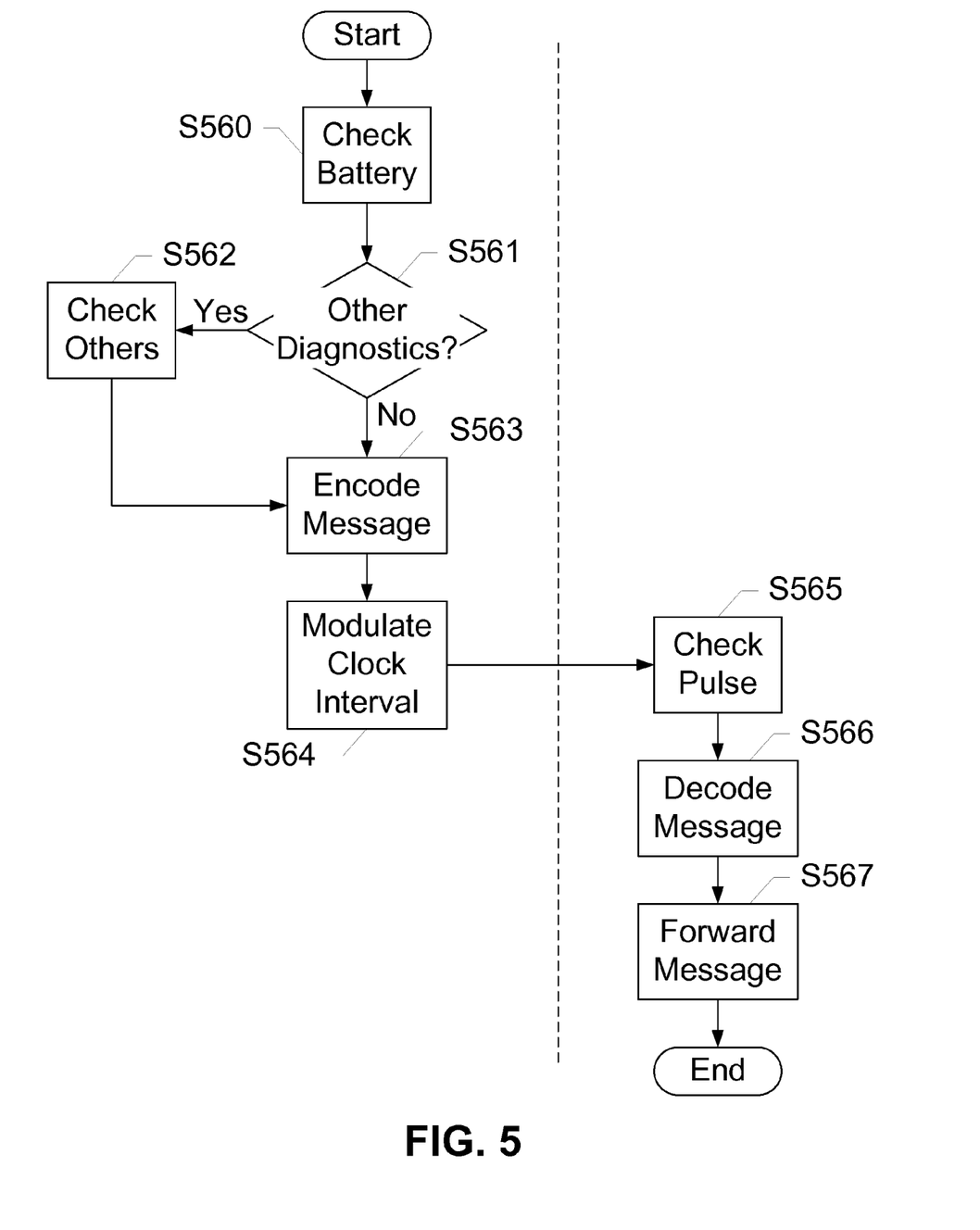
FIG. 5 shows a method of transferring information from a cardiac pacemaker, according to an exemplary embodiment of the subject disclosure.

FIG. 5 shows a method for transferring information from a cardiac pacemaker to a message decoder, according to an exemplary embodiment of the subject disclosure. In this embodiment, logic on the cardiac pacemaker checks a level of a battery S560. The logic then determines whether any other diagnostics are necessary S561. These diagnostics include an analysis of the performance of the cardiac pacemaker, or may be received from any device in communication with the cardiac pacemaker. If other diagnostics are necessary, the other diagnostics are checked S562. With all desired diagnostics checked, or if no diagnostics are needed, the logic on the cardiac pacemaker is used to encode a message containing all received diagnostic information S563. The message is encoded by modulating a clock interval of the cardiac pacemaker S564 with one or more sub-intervals as described herein. The modulation of the clock interval causes the muscle stimulator to stimulate the sinoatrial node of the heart, resulting in a heartbeat corresponding to the modulated clock.

A monitoring device such as a pulse monitor or a blood-pressure monitor checks the pulse of the patient S565. A message decoder in communication with the monitoring device decodes the message S566. The message decoder may be included within the monitoring device, or within a mobile device in communication with the monitoring device, etc. The message is then forwarded S567 to a physician center, to a mobile device, to a wireline device, etc. over a wireless or wired connection.

In some embodiments, when the pacemaker checks connected devices for diagnostics, the connected device performs its own diagnostics and performance and sends the results in a message to the pacemaker. This message can be raw, requiring encoding, or already encoded and ready to be sent through the pulse of the patient. Communication between electronic devices uses binary encoding often. However, the connected device may encode differently than the pacemaker and the pulse monitor. Encoding may have to be translated in embodiments with connected devices of different binary encoding schemes.

Figures 6A, 6B:
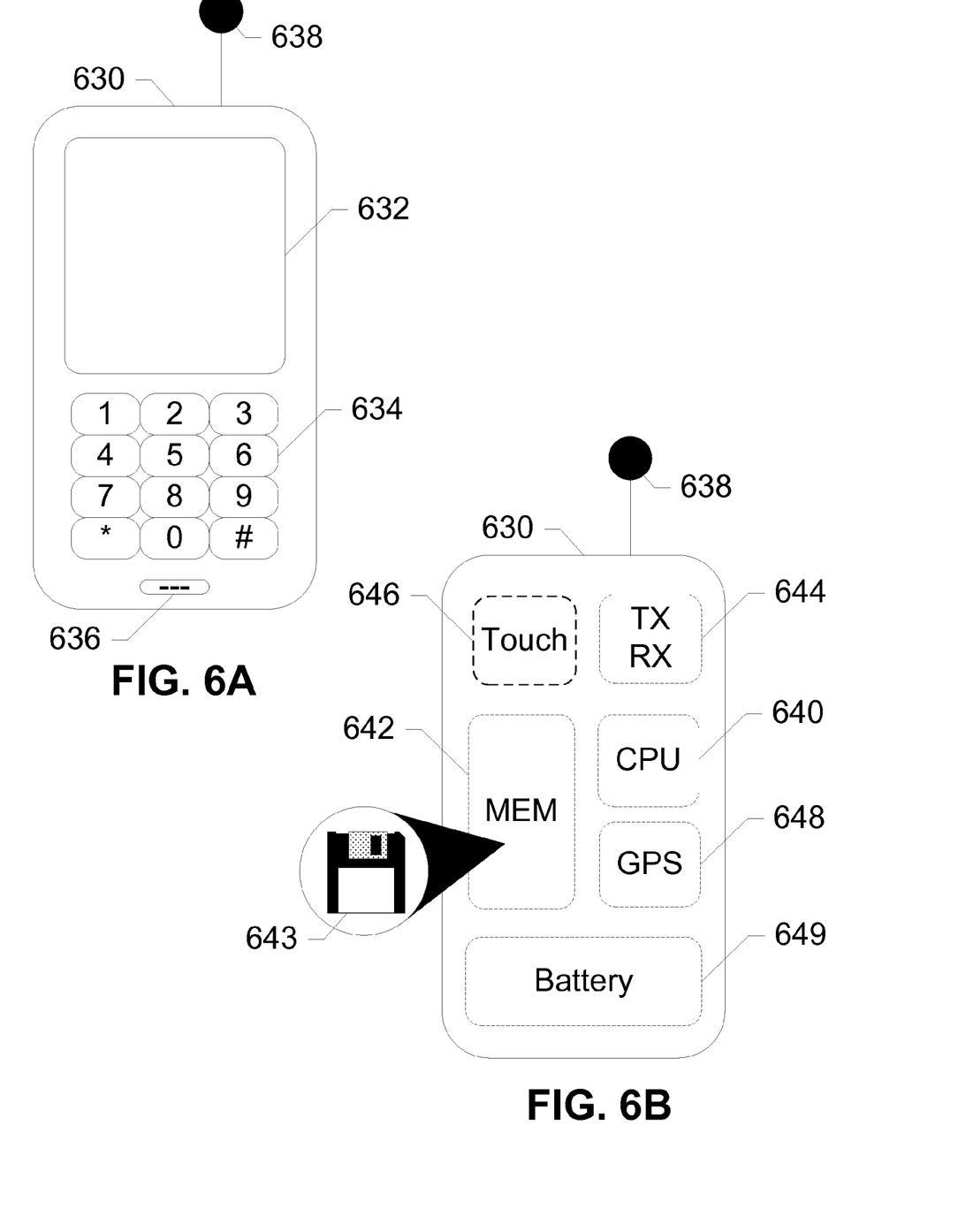
FIGS. 6A and 6B respectively show the external and internal components of a mobile device, according to an exemplary embodiment of the subject disclosure.

FIGS. 6A and 6B respectively show the external and internal components of a mobile device 630, according to an exemplary embodiment of the subject disclosure. Mobile device 630 includes a display 632, a keypad 634, a microphone 636, and an antenna 638. Mobile device 630 further includes a transceiver 644, a touch sensor 646, a battery 648, a central processing unit (CPU) 640, and a memory 642. Display 632 is an LCD, LED or other type of display on which a patient can view selections, numbers, letters, etc. Display 632 allows the patient to view messages being created or received, view contacts, view dialed numbers, etc. Display 632 may also be a touch screen, thereby being used as an input device as well. In embodiments not using a touch screen, a keypad is typically used as an input device, for instance, to type a telephone number or a message. Such a keypad may be a numerical keypad, a QWERTY keyboard, etc. Microphone 636 allows the patient to verbally communicate with others using mobile device 630. Antenna 638 is a transducer designed to transmit or receive electromagnetic waves to and from a network.

In conjunction with antenna 638, transceiver 644 allows mobile device 630 to wirelessly communicate with a cellular network or with other mobile devices across the cellular network, using near field communications, etc. Transceiver 644 may be a cellular transceiver, wireless transceiver, etc., and includes combinations of transceivers to communicate with assorted wireless networks. Battery 649 provides power to each of the components of mobile device 630, and can include an interface to an external power supply. CPU 640 controls components of mobile device 630 according to instructions in logic 643 stored on memory 642. Memory 642 comprises any computer readable medium, such as RAM, ROM, etc. A GPS receiver 648 enables location determination to facilitate location-based services for mobile device 630.

In some embodiments, the mobile device is capable of reading the pulse of the patient without the need for a separate pulse monitoring device. These mobile devices are equipped with a pulse sensor such as a touch screen, etc. Two-way capacitive transducers and other touch screen technologies can detect a variety of human stimuli including the conductivity of skin; the specific motions associated with natural muscular twitches; the pressure variations associated with pulse; the temperature of skin; etc. Such technologies use a variety of means and metrics to detect these stimuli, including galvanic response for measuring skin conductivity, and are included in commonly owned U.S. patent application Ser. No. 12/334,377, which is hereby incorporated by reference in its entirety. This way, the mobile device reads the pulse and decodes the message for forwarding to the physician server, home server, etc. However, some messages may take several minutes to transmit from the pacemaker to the mobile device. Therefore separate pulse monitors and mobile devices are used for longer messages. The pulse monitor may be worn in a way such that it makes constant contact with the patient's wrist, neck, or skin in some other position capable of constant pulse monitoring. As a result, the patient does not have to actively check the pulse with the mobile device. The worn pulse monitor can receive messages passively and alert the patient when necessary. Many mobile devices run standard operating systems such as 105, ANDROID, WINDOWS MOBILE, SYMBIAN, etc. Exemplary embodiments of the logic on the memory are capable of running under these operating systems.

Figure 7:
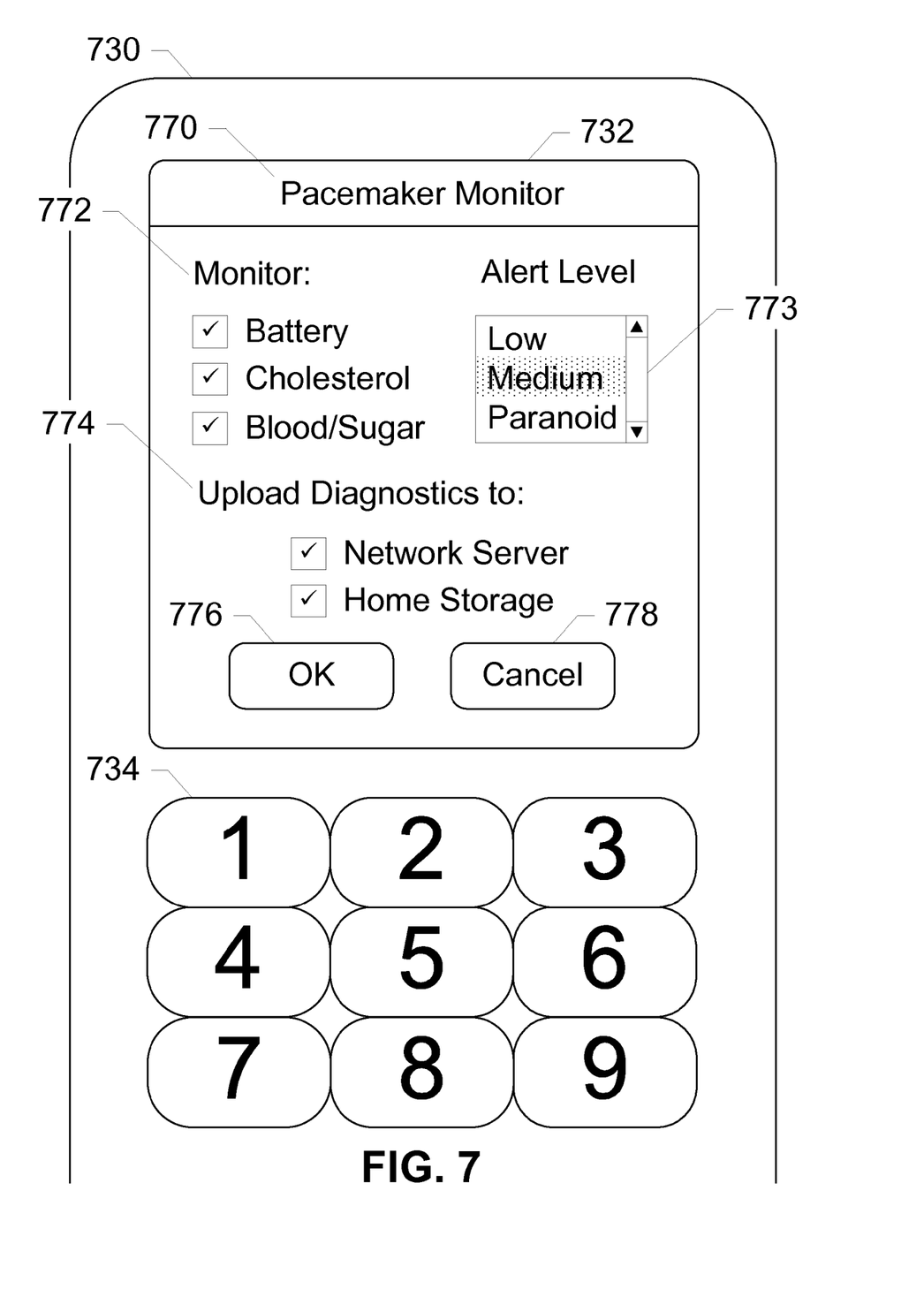
FIG. 7 shows a pacemaker monitor application on a mobile device, according to an exemplary embodiment of the subject disclosure.

FIG. 7 shows a pacemaker monitor application 770 on a mobile device 730, according to an exemplary embodiment of the subject disclosure. Pacemaker monitor 770 includes a monitoring selection 772, an alert level 773, an upload location 774, an OK button 776 and a Cancel button 778. Monitoring selection 772 allows the patient to select which performance or health attributes to monitor. Among the choices are the pacemaker battery, the patient's cholesterol, and the patient's blood/sugar level. With all of these choices checked, mobile device 730 will monitor messages from the pacemaker concerning the pacemaker battery, the patient's cholesterol level, and the patient's blood/sugar level. Other options are possible and will be apparent to those having ordinary skill in the art in light of this disclosure.

Alert level 773 enables the patient to determine when and how to be alerted. In this embodiment, the selections include low, medium, and paranoid. Each setting may be linked to a separate alert tone, level, and method. Other embodiments may allow more detailed settings, such as per monitor alert levels. Upload location 774 enables the patient to select which server or network location to archive messages. The network server is most likely a physician server, while the home storage is most likely a home backup server. When the patient has changed any of the settings on the screen, the patient activates OK button 776 to save the changes and continue using mobile device 730. If the patient has made changes, but does not wish to save them, then the patient activates Cancel button 778. Buttons 776 and 778 are activated using keypad 734 or touch screen 732.

The foregoing disclosure of the exemplary embodiments of the subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. For instance, communication between mobile devices and network elements can be accomplished by Internet Protocol (IP) addressing, Session Initiation Protocol (SIP) signaling over an IP Multimedia System (IMS), Voice over IP (VoIP), etc. The scope of the subject disclosure is to be defined only by the claims appended hereto, and by their equivalents.

Further, in describing representative embodiments of the subject disclosure, the specification may have presented the method and/or process of the subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the subject disclosure should not be limited to the performance of their steps in the order written, and one skilled in the art can readily appreciate that the sequences may be varied and still remain within the spirit and scope of the subject disclosure.

What is claimed is:

1. A method comprising:
applying, by a system comprising a cardiac pacemaker and an externally wearable monitor, a standard interval clock of the cardiac pacemaker to stimulate a heartbeat;
receiving, by the system, a signal from an internal device separate from the cardiac pacemaker, the cardiac pacemaker and the internal device both disposed within a patient's body, the internal device electrically coupled to the cardiac pacemaker, the signal representing information regarding a measurable aspect of the patient's body;
modifying, by the system, a standard interval of the standard interval clock by adding or subtracting a subinterval to generate a modified interval to represent a binary digit, thereby encoding the information as an encoded binary message;

stimulating, by the system, a heart muscle according to the modified interval to cause a pulse at the modified interval including the encoded binary message; and monitoring, by the system, the pulse to measure timing of the pulse to distinguish modified and unmodified pulse intervals and thereby receive the encoded binary message; and displaying, by the system, a decoded message including the information, wherein the monitor comprises a decoder for generating the decoded message or a memory for storing the encoded binary message for subsequent transmission to a decoding device remote from the monitor, wherein the monitoring is performed according to a predetermined schedule using a systolic blood pressure sensor of the externally wearable monitor, wherein the monitoring comprises performing an error checking procedure whereby an information content of the binary message is reduced, and wherein an error is characterized by contraction of the heart muscle at a rate other than that provided by the pacemaker, wherein the measurable aspect comprises a level of sugar, cholesterol, insulin, iron, or any combination thereof, wherein a lengthened modified interval generated by adding the subinterval to the standard interval represents a first binary value, and a shortened modified interval generated by subtracting the subinterval from the standard interval represents a second binary value that is opposite of the first binary value.

2. The method in claim 1, further comprising receiving, by the system via the monitor, a plurality of binary digits from the heartbeat, wherein the binary message has a bit rate given by an average heartbeat rate.

3. The method in claim 2, further comprising decoding, by the system, the binary message from the plurality of binary digits.

4. The method in claim 3, further comprising sending, by the system, the binary message to a wireless communication device.

5. The method in claim 3, further comprising sending, by the system, the binary message to a medical monitoring server.

6. The method in claim 1, wherein the cardiac pacemaker comprises a battery, and further comprising monitoring, by the system, a life of the battery.

7. The method in claim 6, further comprising encoding, by the system, a binary message regarding the life of the battery.

8. The method in claim 7, wherein the system further comprises a wireless communication device, and further comprising alerting, by the system, the patient on the wireless communication device when a binary message is received indicating a low battery life.

9. A device comprising:

a standard interval clock of a cardiac device for stimulating a heartbeat;

an electric coupling for receiving a signal from an internal device separate from the cardiac device, the cardiac device and the internal device both disposed within a patient's body, the signal representing information regarding a measurable aspect of the patient's body;

a clock modulator for modifying a standard interval of the standard interval clock by adding or subtracting a subinterval to generate a modified interval to represent a binary digit and thereby encoding the information as an encoded binary message; and a muscle stimulator for stimulating a heart muscle according to the modified interval to cause a pulse at the modified interval including the encoded binary message; and an externally wearable monitor for monitoring the pulse to measure timing of the pulse to distinguish modified and unmodified pulse intervals, thereby receiving the encoded binary message, wherein the externally wearable monitor comprises a systolic blood pressure sensor and a display device for displaying a decoded message including the information, wherein the externally wearable monitor comprises a decoder for generating the decoded message or a memory for storing the encoded binary message for subsequent transmission to a decoding device remote from the externally wearable monitor, wherein the externally wearable monitor monitors the pulse according to a predetermined schedule, wherein the externally wearable monitor performs an error checking procedure whereby an information content of the binary message is reduced, and wherein an error is characterized by contraction of the heart muscle at a rate other than that provided by the muscle stimulator, wherein the measurable aspect comprises a level of sugar, cholesterol, insulin, iron, or any combination thereof, wherein a lengthened modified interval formed by adding the subinterval to the standard interval represents a first binary value, and a shortened modified interval formed by subtracting the subinterval from the standard interval represents a second binary value that is opposite of the first binary value.

10. The device in claim 9, further comprising a performance monitor.

11. The device in claim 10, further comprising a battery, wherein the performance monitor monitors a life of the battery.

12. The device in claim 9, wherein the monitoring is performed during a rest period.

* * * * *